United States Patent
Lockwood et al.

(10) Patent No.: US 7,338,482 B2
(45) Date of Patent: Mar. 4, 2008

(54) EXTERNAL CATHETER ACCESS TO VACUUM BANDAGE

(75) Inventors: Jeffrey S. Lockwood, Batesville, IN (US); Robert Petrosenko, Batesville, IN (US)

(73) Assignee: Hill-Rom Services, Inc., Wilmington, DE (US)

(*) Notice: Subject to any disclaimer, the term of this patent is extended or adjusted under 35 U.S.C. 154(b) by 273 days.

(21) Appl. No.: 10/505,833

(22) PCT Filed: Dec. 20, 2002

(86) PCT No.: PCT/US02/41300

§ 371 (c)(1),
(2), (4) Date: Aug. 26, 2004

(87) PCT Pub. No.: WO03/073970

PCT Pub. Date: Sep. 12, 2003

(65) Prior Publication Data

US 2005/0085795 A1    Apr. 21, 2005

Related U.S. Application Data

(60) Provisional application No. 60/360,405, filed on Feb. 28, 2002.

(51) Int. Cl.
*A61M 27/00* (2006.01)
*A61M 1/00* (2006.01)
*A61M 25/00* (2006.01)
*A61F 5/44* (2006.01)
*A61H 7/00* (2006.01)

(52) U.S. Cl. ............. 604/543; 604/313; 604/317; 604/326; 604/327; 604/355; 604/523; 604/533; 601/6

(58) Field of Classification Search ........... 604/192, 604/197, 198, 263, 289, 290, 304, 305, 308, 604/313, 315–317, 322, 326, 327, 355, 523, 604/533, 540, 541, 543; 601/6–14; 602/41
See application file for complete search history.

(56) References Cited

U.S. PATENT DOCUMENTS 774,529 A    11/1904    Nieschang (Continued)

FOREIGN PATENT DOCUMENTS

CA    2303085    3/1999

(Continued)

OTHER PUBLICATIONS

A New Method for Fixation of Drainage Catheters, BJJ Abdullah, J HK Coll Radiol 2001; 4:272-273.*

(Continued)

*Primary Examiner*—Tatyana Zalukaeva
*Assistant Examiner*—Michael G Bogart
(74) *Attorney, Agent, or Firm*—Barnes & Thornburg LLP

(57) ABSTRACT

A bandage is provided for use with a wound having a wound surface. The bandage is connectable to a vacuum source and may include a flexible cover positioned over the wound and a collar coupled to the cover. The cover includes a port and is configured to seal to a patient's healthy skin surrounding the wound. The collar may be coupled to the cover and include a passageway in communication with the port of the cover. The passageway is configured to receive at least a portion of a tube in communication with the vacuum source. The bandage may also include a sealer coupled to the collar. The sealer may be configured to provide a substantially airtight seal between the tube and the passageway to create a sealed environment capable of maintaining a negative pressure between the cover and the wound surface.

12 Claims, 5 Drawing Sheets

U.S. PATENT DOCUMENTS

| | | |
|---|---|---|
| 1,000,001 A | 8/1911 | Holz |
| 1,355,846 A | 10/1920 | Rannells |
| 1,385,346 A | 7/1921 | Taylor |
| 1,709,520 A | 4/1929 | Chandler |
| 1,936,129 A | 11/1933 | Fisk |
| 2,078,180 A | 4/1937 | Kronenberg |
| 2,195,771 A | 4/1940 | Estler |
| 2,221,758 A | 11/1940 | Elmquist |
| 2,338,339 A | 1/1944 | LaMere et al. |
| 2,443,481 A | 6/1948 | Sene |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans et al. |
| 3,026,874 A | 3/1962 | Stevens |
| 3,315,665 A | 4/1967 | MacLeod |
| 3,367,332 A | 2/1968 | Groves |
| 3,382,867 A | 5/1968 | Reaves |
| 3,492,991 A | 2/1970 | Dyer, Jr. |
| 3,520,300 A | 7/1970 | Flower, Jr. |
| 3,528,416 A | 9/1970 | Chamberlain |
| 3,568,675 A | 3/1971 | Harvey |
| 3,585,742 A | 6/1971 | Tyler |
| 3,599,639 A | 8/1971 | Spotz |
| 3,610,238 A | 10/1971 | Rich, Jr. |
| 3,648,692 A | 3/1972 | Wheeler |
| 3,683,894 A | 8/1972 | Villari |
| 3,721,244 A | 3/1973 | Elmaleh |
| 3,752,158 A | 8/1973 | Kariher |
| 3,782,377 A | 1/1974 | Rychlik |
| 3,812,972 A | 5/1974 | Rosenblum |
| 3,814,095 A | 6/1974 | Lubens |
| 3,831,588 A | 8/1974 | Rindner |
| 3,874,387 A | 4/1975 | Barbieri |
| 3,903,882 A | 9/1975 | Augurt |
| 3,935,863 A | 2/1976 | Kliger |
| 3,954,105 A | 5/1976 | Nordby et al. |
| 3,982,546 A | 9/1976 | Friend |
| 4,013,076 A | 3/1977 | Puderbaugh et al. |
| RE29,319 E | 7/1977 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,178,974 A | 12/1979 | Levin |
| 4,191,204 A | 3/1980 | Nehring |
| 4,224,941 A | 9/1980 | Stivala |
| 4,250,882 A | 2/1981 | Adair |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,399,816 A | 8/1983 | Spangler |
| 4,457,755 A | 7/1984 | Wilson |
| 4,460,370 A | 7/1984 | Allison et al. |
| 4,465,062 A | 8/1984 | Versaggi et al. |
| 4,469,092 A | 9/1984 | Marshall et al. |
| 4,525,166 A | 6/1985 | Leclerc |
| 4,533,352 A | 8/1985 | Van Beek et al. |
| 4,533,419 A | 8/1985 | Pieslak et al. |
| 4,540,412 A | 9/1985 | Van Overloop |
| 4,553,967 A | 11/1985 | Ferguson et al. |
| 4,569,674 A | 2/1986 | Phillips et al. |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielsen |
| 4,624,656 A | 11/1986 | Clark et al. |
| 4,633,863 A | 1/1987 | Filips et al. |
| 4,637,819 A | 1/1987 | Oullette et al. |
| 4,641,643 A | 2/1987 | Greer |
| 4,645,492 A * | 2/1987 | Weeks .................. 604/174 |
| 4,655,210 A | 4/1987 | Edenbaum et al. |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Frysliie |
| 4,679,590 A | 7/1987 | Hergenroeder |
| 4,717,382 A | 1/1988 | Clemens et al. |
| 4,733,659 A | 3/1988 | Edenbaum et al. |
| 4,735,606 A | 4/1988 | Davison |
| 4,735,610 A | 4/1988 | Akkas et al. |
| 4,740,202 A | 4/1988 | Stacey et al. |
| 4,743,232 A | 5/1988 | Kruger |
| 4,747,166 A | 5/1988 | Kuntz |
| 4,759,354 A | 7/1988 | Quarfoot |
| 4,765,316 A | 8/1988 | Marshall |
| 4,778,446 A | 10/1988 | Jensen |
| 4,778,456 A | 10/1988 | Lokken |
| 4,798,578 A | 1/1989 | Ranford |
| 4,820,265 A | 4/1989 | DeSatnick et al. |
| 4,820,284 A | 4/1989 | Hauri |
| 4,834,110 A | 5/1989 | Richard |
| 4,872,450 A | 10/1989 | Austad |
| 4,890,608 A | 1/1990 | Steer |
| 4,897,081 A | 1/1990 | Poirier et al. |
| 4,906,240 A | 3/1990 | Reed et al. |
| 4,915,694 A | 4/1990 | Yamamoto et al. |
| 4,917,112 A | 4/1990 | Kalt |
| 4,921,492 A | 5/1990 | Schultz et al. |
| 4,930,997 A | 6/1990 | Bennett |
| 4,941,882 A | 7/1990 | Ward et al. |
| 4,953,565 A | 9/1990 | Tachibana et al. |
| 4,957,492 A | 9/1990 | McVay |
| 4,962,761 A | 10/1990 | Golden |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,994,022 A | 2/1991 | Steffler et al. |
| 4,997,425 A | 3/1991 | Shioya et al. |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie et al. |
| 5,034,003 A | 7/1991 | Denance |
| 5,034,006 A | 7/1991 | Hosoda et al. |
| 5,035,865 A | 7/1991 | Inaba et al. |
| 5,042,978 A | 8/1991 | Quenin et al. |
| 5,045,777 A | 9/1991 | Itagaki |
| 5,060,662 A | 10/1991 | Farnswoth, III |
| 5,071,409 A | 12/1991 | Rosenberg |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,101,808 A | 4/1992 | Kobayashi et al. |
| 5,106,362 A | 4/1992 | Gilman |
| 5,106,629 A | 4/1992 | Cartmell et al. |
| 5,135,518 A | 8/1992 | Vera |
| 5,146,925 A | 9/1992 | Snow |
| 5,147,338 A | 9/1992 | Lang et al. |
| 5,149,331 A | 9/1992 | Ferdman et al. |
| 5,152,757 A | 10/1992 | Eriksson |
| 5,160,322 A | 11/1992 | Scheremet et al. |
| 5,167,613 A | 12/1992 | Karami et al. |
| 5,170,781 A | 12/1992 | Loomis |
| 5,176,502 A | 1/1993 | Sanderson et al. |
| 5,176,663 A | 1/1993 | Svedman et al. |
| 5,176,667 A | 1/1993 | DeBring |
| 5,189,609 A | 2/1993 | Tivig et al. |

| | | | | | |
|---|---|---|---|---|---|
| 5,215,539 A | 6/1993 | Schoolman | 5,986,163 A | 11/1999 | Augustine |
| 5,228,431 A | 7/1993 | Giarretto | 6,010,527 A | 1/2000 | Augustine et al. |
| 5,230,350 A | 7/1993 | Fentress | 6,017,493 A | 1/2000 | Cambron et al. |
| 5,238,654 A | 8/1993 | Nohl et al. | 6,039,724 A | 3/2000 | Seifert et al. |
| 5,261,893 A | 11/1993 | Zamierowski | 6,045,518 A | 4/2000 | Augustine |
| 5,263,922 A | 11/1993 | Sova et al. | 6,045,541 A | 4/2000 | Matsumoto et al. |
| 5,265,605 A | 11/1993 | Afflerbach | 6,056,730 A | 5/2000 | Greter |
| 5,291,887 A | 3/1994 | Stanley et al. | 6,071,254 A | 6/2000 | Augustine |
| 5,298,015 A | 3/1994 | Komatsuzaki et al. | 6,071,267 A | 6/2000 | Zamierowski |
| 5,306,298 A | 4/1994 | Godley, III et al. | 6,071,304 A | 6/2000 | Augustine et al. |
| 5,330,452 A | 7/1994 | Zook | 6,080,189 A | 6/2000 | Augustine et al. |
| 5,344,415 A | 9/1994 | DeBusk et al. | 6,080,243 A | 6/2000 | Insley et al. |
| 5,349,965 A | 9/1994 | McCarver | 6,093,160 A | 7/2000 | Augustine et al. |
| 5,358,494 A | 10/1994 | Svedman | 6,093,230 A | 7/2000 | Johnson et al. |
| 5,374,254 A | 12/1994 | Buma | 6,095,992 A | 8/2000 | Augustine |
| 5,376,252 A | 12/1994 | Eckstrom et al. | 6,110,197 A | 8/2000 | Augustine et al. |
| 5,380,280 A | 1/1995 | Peterson | 6,113,561 A | 9/2000 | Augustine |
| 5,395,315 A | 3/1995 | Griep | 6,117,111 A | 9/2000 | Fleischmann |
| 5,419,768 A | 5/1995 | Kayser | 6,135,116 A | 10/2000 | Vogel et al. |
| 5,431,622 A | 7/1995 | Pyrozyk et al. | 6,142,982 A | 11/2000 | Hunt et al. |
| 5,437,651 A | 8/1995 | Todd et al. | 6,143,945 A | 11/2000 | Augustine et al. |
| 5,445,604 A | 8/1995 | Lang | 6,149,614 A | 11/2000 | Dunshee et al. |
| 5,451,215 A | 9/1995 | Wolter | 6,174,306 B1 | 1/2001 | Fleischmann |
| 5,478,333 A | 12/1995 | Asherman, Jr. | 6,203,563 B1 | 3/2001 | Fernandez |
| 5,484,420 A | 1/1996 | Russo | 6,207,875 B1 | 3/2001 | Lindqvist et al. |
| 5,484,427 A | 1/1996 | Gibbons | 6,213,965 B1 | 4/2001 | Augustine et al. |
| 5,484,428 A | 1/1996 | Drainville et al. | 6,213,966 B1 | 4/2001 | Augustine |
| 5,487,889 A | 1/1996 | Eckert et al. | 6,217,535 B1 | 4/2001 | Augustine |
| 5,520,652 A | 5/1996 | Peterson | 6,235,009 B1 | 5/2001 | Skow |
| 5,527,293 A | 6/1996 | Zamierowski | 6,235,047 B1 | 5/2001 | Augustine et al. |
| 5,531,670 A | 7/1996 | Westby et al. | 6,241,697 B1 | 6/2001 | Augustine |
| 5,533,981 A | 7/1996 | Mandro et al. | 6,241,698 B1 | 6/2001 | Augustine |
| 5,534,346 A | 7/1996 | Robinson | 6,244,311 B1 | 6/2001 | Hand et al. |
| 5,542,918 A | 8/1996 | Atkinson | 6,248,084 B1 | 6/2001 | Augustine et al. |
| 5,549,584 A | 8/1996 | Gross | 6,254,557 B1 | 7/2001 | Augustine et al. |
| 5,556,375 A | 9/1996 | Ewall | 6,254,580 B1 | 7/2001 | Svedman |
| 5,578,022 A | 11/1996 | Scherson et al. | 6,264,622 B1 | 7/2001 | Augustine |
| 5,607,388 A | 3/1997 | Ewall | 6,264,979 B1 | 7/2001 | Svedman |
| 5,624,418 A | 4/1997 | Shepard | 6,267,740 B1 | 7/2001 | Augustine et al. |
| 5,628,735 A | 5/1997 | Skow | 6,283,931 B1 | 9/2001 | Augustine |
| 5,635,201 A | 6/1997 | Fabo | 6,284,941 B1 | 9/2001 | Cox et al. |
| 5,636,643 A | 6/1997 | Argenta et al. | 6,290,685 B1 | 9/2001 | Insley et al. |
| 5,645,081 A | 7/1997 | Argenta et al. | 6,293,917 B1 | 9/2001 | Augustine et al. |
| 5,655,258 A | 8/1997 | Heintz | 6,345,623 B1 | 2/2002 | Heaton et al. |
| 5,656,027 A | 8/1997 | Ellingboe | 6,398,767 B1 | 6/2002 | Fleischmann |
| 5,662,598 A | 9/1997 | Tobin | 6,458,109 B1 | 10/2002 | Henley et al. |
| 5,662,624 A | 9/1997 | Sundstrom et al. | 6,471,685 B1 | 10/2002 | Johnson |
| 5,662,625 A | 9/1997 | Westwood | 6,472,581 B1 | 10/2002 | Muramatsu et al. |
| 5,669,892 A | 9/1997 | Keogh et al. | 6,491,682 B2 | 12/2002 | Paderni |
| 5,672,152 A | 9/1997 | Mason et al. | 6,553,998 B2 | 4/2003 | Heaton et al. |
| 5,678,564 A | 10/1997 | Lawrence et al. | 6,599,277 B2 | 7/2003 | Neubert |
| 5,690,815 A | 11/1997 | Krasnoff et al. | 6,626,891 B2 | 9/2003 | Ohmstede |
| 5,697,920 A | 12/1997 | Gibbons | 6,638,270 B2 | 10/2003 | Johnson |
| 5,718,955 A | 2/1998 | McGuire et al. | 6,648,862 B2 | 11/2003 | Watson |
| 5,735,833 A | 4/1998 | Olson | 6,663,349 B1 | 12/2003 | Discenzo et al. |
| 5,741,237 A | 4/1998 | Walker | 6,685,681 B2 | 2/2004 | Lockwood et al. |
| 5,759,570 A | 6/1998 | Arnold | 6,691,047 B1 | 2/2004 | Fredericks |
| 5,762,640 A | 6/1998 | Kajiwara et al. | 6,695,823 B1 | 2/2004 | Lina et al. |
| 5,782,871 A | 7/1998 | Fujiwara et al. | 6,749,592 B2 | 6/2004 | Lord |
| 5,817,145 A | 10/1998 | Augustine et al. | 6,752,794 B2 | 6/2004 | Lockwood et al. |
| 5,827,246 A | 10/1998 | Bowen | 6,755,807 B2 | 6/2004 | Risk, Jr. et al. |
| 5,827,296 A | 10/1998 | Morris et al. | 6,764,462 B2 | 7/2004 | Risk, Jr. et al. |
| 5,881,723 A | 3/1999 | Wallace et al. | 6,800,074 B2 | 10/2004 | Henley et al. |
| 5,911,222 A | 6/1999 | Lawrence et al. | 6,814,079 B2 | 11/2004 | Heaton et al. |
| 5,919,476 A | 7/1999 | Fischer et al. | 6,824,533 B2 | 11/2004 | Risk, Jr. et al. |
| 5,921,972 A | 7/1999 | Skow | 6,855,135 B2 | 2/2005 | Lockwood et al. |
| 5,928,174 A | 7/1999 | Gibbins | 7,022,113 B2 | 4/2006 | Lockwood et al. |
| 5,941,859 A | 8/1999 | Lerman | 2001/0029956 A1 | 10/2001 | Argenta et al. |
| 5,947,914 A | 9/1999 | Augustine | 2001/0043943 A1 | 11/2001 | Coffey |
| 5,954,680 A | 9/1999 | Augustine | 2002/0065494 A1 | 5/2002 | Lockwood et al. |
| 5,961,480 A | 10/1999 | Augustine | 2002/0082668 A1 | 6/2002 | Ingman |
| 5,964,721 A | 10/1999 | Augustine | 2002/0115952 A1 | 8/2002 | Johnson et al. |
| 5,964,723 A | 10/1999 | Augustine | 2002/0161317 A1 | 10/2002 | Risk et al. |

| | | | |
|---|---|---|---|
| 2002/0193723 A1 | 12/2002 | Batdorf, Sr. et al. | |
| 2003/0208149 A1 | 11/2003 | Coffey | |
| 2004/0030304 A1 | 2/2004 | Hunt | |
| 2004/0064111 A1 | 4/2004 | Lockwood et al. | |
| 2004/0243073 A1 | 12/2004 | Lockwood et al. | |
| 2004/0249353 A1 | 12/2004 | Risks, Jr. et al. | |
| 2005/0004534 A1 | 1/2005 | Lockwood et al. | |
| 2005/0010153 A1 | 1/2005 | Lockwood et al. | |
| 2005/0070858 A1 | 3/2005 | Lockwood et al. | |
| 2005/0085795 A1 | 4/2005 | Lockwood et al. | |
| 2005/0090787 A1 | 4/2005 | Risk, Jr. et al. | |
| 2005/0131327 A1 | 6/2005 | Lockwood et al. | |
| 2006/0015087 A1 | 1/2006 | Risk, Jr. et al. | |
| 2006/0029650 A1 | 2/2006 | Coffey | |
| 2006/0041247 A1 | 2/2006 | Petrosenko et al. | |
| 2006/0129137 A1 | 6/2006 | Lockwood et al. | |
| 2007/0005028 A1 | 1/2007 | Risk, Jr. et al. | |

FOREIGN PATENT DOCUMENTS

| | | |
|---|---|---|
| DE | 372727 | 3/1923 |
| DE | 28 09 828 A1 | 9/1978 |
| DE | 3102674 A1 | 9/1982 |
| DE | 3539533 A1 | 5/1987 |
| DE | 4111122 A1 | 4/1993 |
| DE | 29504378 U1 | 10/1995 |
| DE | 19722075 C1 | 10/1998 |
| DK | 64055 | 10/1945 |
| EP | 0117632 A2 | 9/1984 |
| EP | 0424165 A1 | 4/1991 |
| EP | 0485657 A1 | 5/1992 |
| EP | 0547496 A1 | 6/1993 |
| EP | 0853 950 A1 | 7/1998 |
| EP | 0 777 504 B1 | 10/1998 |
| EP | 0 880 953 A2 | 12/1998 |
| EP | 1 088 569 A2 | 4/2001 |
| FR | 500253 | 3/1920 |
| FR | 1303238 | 7/1962 |
| GB | 3090 | 6/1902 |
| GB | 641061 | 8/1950 |
| GB | 1549756 | 8/1979 |
| GB | 1584772 | 2/1981 |
| GB | 2220357 A | 1/1990 |
| GB | 2307180 | 5/1997 |
| GB | 2329127 A | 3/1999 |
| GB | 2333965 A | 8/1999 |
| GB | 2336546 A | 10/1999 |
| GB | 2342584 A | 4/2000 |
| GB | 2344531 A | 6/2000 |
| GB | 2351025 A | 12/2000 |
| HU | 199304 B | 1/1989 |
| HU | 51150 | 4/1990 |
| HU | 205557 B | 4/1990 |
| HU | 76351 | 8/1997 |
| HU | 215563 B | 8/1997 |
| SE | 84485 | 10/1935 |
| SU | 587941 | 1/1978 |
| SU | 1268175 A1 | 11/1986 |
| WO | WO 89/04158 | 5/1989 |
| WO | WO 90/11795 | 10/1990 |
| WO | WO 91/00718 | 1/1991 |
| WO | WO 91/16030 | 10/1991 |
| WO | WO92/19313 | 11/1992 |
| WO | WO 92/20299 | 11/1992 |
| WO | WO 93/09727 | 5/1993 |
| WO | WO 94/00090 | 1/1994 |
| WO | WO 94/20041 | 9/1994 |
| WO | 9605873 | 2/1996 |
| WO | WO 96/05873 | 2/1996 |
| WO | WO 96/15745 | 5/1996 |
| WO | WO97/18007 | 5/1997 |
| WO | 9838944 | 9/1998 |
| WO | 9901173 | 1/1999 |
| WO | WO 99/13793 | 3/1999 |
| WO | 9959816 | 11/1999 |
| WO | WO 00/07653 | 2/2000 |
| WO | WO 00/15277 | 3/2000 |
| WO | 0021586 | 4/2000 |
| WO | WO 00/21586 | 4/2000 |
| WO | WO 00/26100 | 5/2000 |
| WO | WO 00/30567 | 6/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 01/49233 A1 | 7/2001 |
| WO | 0185248 | 11/2001 |
| WO | 0189431 | 11/2001 |
| WO | WO 01/85248 A1 | 11/2001 |
| WO | WO 01/89431 | 11/2001 |
| WO | 03005943 | 1/2003 |
| WO | 03045492 | 6/2003 |

OTHER PUBLICATIONS

Davydov, et al., Vestn. Khir., Sep. 1988—"Vacuum Therapy in the Treatment of Acute Suppurative Diseases Of Soft Tissues and Suppurative Wounds" (English translation by R. McElroy Translation Co., Austin, Texas.

Davydov, et al., Khirurgiia, Jun. 1990—"Pathogenic Mechanism of the Effect of Vacuum Therapy on the Course of the Wound Process" (English translation by R. McElroy Translation Co., Austin, Texas).

Davydov, et al., Vestn. Khir., Nov. 1986—"Vacuum Therapy in the Treatment of Suppurative Lactation Mastitis" (English translation by R. McElroy Translation Co., Austin, Texas).

Davydov, et al. Vestn. Khir., Oct. 1988—"Bacteriological and Cytological Evaluation of the Vacuum Therapy of Suppurative Wounds" (English translation by R. McElroy Translation Co., Austin, Texas).

Davydov, et al., Vestn. Khir., Mar. 1990—"Basis of the Use of Forced Early Secondary Suture in the Treatment of Suppurative Wounds by t he Vacuum Therapy Method" (English translation by R. McElroy Translation Co., Austin, Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Venerol., Aug. 1965—"Vacuum Therapy of Some Skin Diseases" (Englsih translation by R. McElroy Translation Co., Austin, Texas).

Jeter, et al., Chronic Wound Care; 27: pp. 240-246—"Managing Draining Wounds and Fistulae: New and Established Methods".

Mulder, et al., Wound Healing Publications 1991—"Clinicians'Pocket Guide to Chronic Wound Repair".

Valenta, AIN Apr. 1994; pp. 44-45—"Using the Vacuum Dressing Alternative for Difficult Wounds".

Wolthuis, et al., Physiological Reviews Jul. 1974; vol. 54, No. 3, pp. 566-595—"Physiological Effects of Locally Applied Reduced Pressure in Man".

Fleischmann, WundForum Spezial IHW 1994; pp. 54-55—"Vacuum Sealing for Treatment of Problematical Wounds" (English translation provided).

Bucalo, et al., Wound Repair and Regeneration; Jul.-Sep. 1993; pp. 181-186—"Inhibition of Cell Proliferation by Chronic Wound Fluid".

Olenius, et al., Plastic and Reconstructive Surgery Feb. 1993: pp. 213-215—"Mitotic Activity in Expanded Human Skin".

Viljanto, et al., Br. J. Surg. 1976; vol. 63: pp. 427-430—"Local Hyperalimentation of Open Wounds".

Dunlop, et al., Br. J. Surg. May 1990; vol. 77: pp. 562-563—"Vacuum Drainage of Groin Wounds after Vascular Surgery: A Controlled Trial".

Comment-Ruckley et al., Apr. 1991, pp. 505-506 on "Vacuum Drainage of Groin Wounds after Vascular Surgery".

Landis, et al., Alternate Suction and Pressure, pp. 925-961—"The Effects of Alternative Suction and Pressure on Blood Flow to the Lower Extremities".

Morykwas, et al., Extracellular Matrix and Healing 1993; pp. 800—"Use of Negative Pressure to Increase the Rate of Granulation Tissue Formation in Chronic Open Wounds".

Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds"; Feb. 11, 1999; 16 pages.

Chariker, et al., Contemporary Surgery Jun. 1989; vol. 34: pp. 59-63—"Effective Management of Incisional and Cutaneous Fistulae with Closed Suction Wound Drainage".

Tittle, et al., Eingag und Annahme des Manuskripts Jan. 7, 1987; pp. 104-107—"New Standards in Postoperative Wound Drainage".

Genecov, et al., Annals of Plastic Surgery Mar. 1998; vol. 40, No. 3: pp. 219-225—"A Controlled Subatmospheric Pressure Dressing Increases the Rate of Skin Graft Donor Site Reepithelialization".

Morykwas, et al., Annals of Plastic Surgery Jun. 1997; vol. 38, No. 6: pp. 553-562—"Vacuum-Assisted Closure: A New Method for Wound Control and Treatment: Animal Studies and Basic Foundation".

Argenta, et al., Annals of Plastic Surgery Jun. 1997; vol. 38, No. 6: pp. 563-577—"Vacuum-Assisted Closure: A New Method for Wound Control and Treatment: Clinical Experience".

Patent Application and Drawings—"Method of Treating Tissue Damage and Apparatus for Same", consisting of 28 pages.

Patent Application and Drawings—"The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499-502—"A New Dressing Method for Free Skin Grafting in Hands".

Medical Industry Week—article "KCI Offers New Treatment for Non-Healing Wounds"; 1 page.

Nakayama, et al., Plast. Reconstr. Surg., Dec. 1990.; vol. 86, No. 6: pp. 1216-1219—"A New Method for the Dressing of Free Skin Grafts".

Sames, Br. Med. J., Nov. 5, 1977; vol. 2, No. 6096: 1123—"Sealing of Wounds with Vacuum Drainage".

Fleishmann, et al., Unfallchirurg 1993; 96:488-492—"Vacuum Sealing for Treatment of Soft Tissue Injury in Open Fractures" (English translation of the Summary provided).

Teder, et al., J. Invest. Surg. 1990; vol. 3: pp.399-407—"Continuous Wound Irrigation in the Pig".

Wood, et al., Br. J. of Surg. 1977; vol. 64: pp. 554-557—"Foam Elastomer Dressing in the Management of Open Granulating Wounds: Experience with 250 Patients".

Neumann, et al., J. of Biomed. Materials Research 1981, vol. 15: pp. 9-18—"Gelatin-Based Sprayable Foam as a Skin Substitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta Physiol. Scand. 1989, vol. 136: pp. 403-409—"Transmission of Externally Applied Negative Pressure to the Underlying Tissue. A Study on the Upper Arm of Man".

Brochure—Aeros—Instavac Aspirator; 1 page.

Brochure—Pleur-evac Adult-Pediatric-Non-Metered Disposable "3-Bottle" Unit, A-4000; 6 pages.

Brochure—Hiblow Air Pump; 1 page.

Brochure—Aeros—Care-E-Vac; 2 pages.

One page brochure—Aeros—Moblvacll.

Brochure/Instruction Manual—Creative Medical Laboratories, Inc.—TUGS (Transportable Universal Gradient Suction) System.

Brochure—Wells Johnson Company—Point 5 Aspirator; 2 pages.

Brochure—Microtek Heritage, Inc.—The Wound-Evac ET, Closed Wound Suction System; 4 pages.

Brochure—KCI—The V.A.C. (Vacuum Assisted Closure), Nov. 5, 1998; 7 pages.

Brochure—Augustine Medical, Warm-Up Active Wound Therapy Wound Covers, 1999; 3 pages.

Brochure—Series 55—Emerson Post-Operative Suction Pumps; 1 page.

Brochure—Emerson Transport Suction Unit; 1 page.

International Search Report for WO 03045492, Lockwood et al., Jun. 2003.

* cited by examiner

EXTERNAL CATHETER ACCESS TO VACUUM BANDAGE

CROSS-REFERENCE TO RELATED APPLICATIONS

This application is a U.S. national counterpart application of International application Ser. No. PCT/US02/41300 filed Dec. 20, 2002, which claims the benefit of U.S. provisional application Ser. No. 60/360,405 filed Feb. 28, 2002.

BACKGROUND OF THE INVENTION

The present disclosure relates to bandages for wounds, and more particularly to the provision of bandages for use with a vacuum and/or irrigation source. Specifically, the present disclosure relates to external catheter access to a wound through the bandage.

The prior art contemplates that chronic wounds may be treated by providing a vacuum in the space above the wound to promote healing. A number of prior art references teach the value of the vacuum bandage or the provision of vacuum in the space above the surface of a chronic wound.

A vacuum bandage is a bandage having a cover for sealing about the outer perimeter of the wound and under which a vacuum is established to act on the wound surface. Applying vacuum to the wound surface promotes healing of chronic wounds. Typically, suction tubes are provided for drawing exudate away from the wound and for creating vacuum under the cover. If the cover is a flexible cover, which is typically more comfortable for the patient, a packing may be provided under the cover to fill the space in which the vacuum is formed. It will be appreciated, however, that the packing will be omitted by many caregivers, and it may be preferable not to have packing.

The following U.S. Patents establish the nature of vacuum treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum treatment of wounds.

As shown, for example, in U.S. Pat. No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section, and tubing to adhere to the skin surrounding the wound in order to form a seal that allows the creation of a vacuum when the suction pump is operating. The '081 patent further teaches use of negative pressure between about 0.1 and 0.99 atmospheres and that the pressure can be substantially continuous and is relieved only to change the dressing on the wound. Alternatively, the '081 patent teaches use of a cyclic application of pressure in alternating periods of application and non-application. In a preferred embodiment, pressure is applied in five-minute periods of application and non-application.

Various other prior art references teach the value of the vacuum bandage or the provision of vacuum to the surface of a chronic wound. Several Russian language articles exist which establish the efficacy of vacuum therapy in the 1980's. Examples of such prior art articles, each of which discusses the use of application of vacuum to a wound to promote healing, are as follows: "Vacuum therapy in the treatment of acute suppurative diseases of soft tissues and suppurative wounds", Davydov, et al., Vestn, Khir., September 1988 (The September 1988 article); "Pathenogenic mechanism of the effect of vacuum therapy on the course of the wound process", Davydov, et al. Khirurigiia, June 1990 (the June 1990 article); and "Vacuum therapy in the treatment of suppurative lactation mastitis", Davydov, et al. Vestn. Khir., November 1986 (the November 1986 article).

The Russian articles distinguish wound drainage from use of vacuum therapy for healing. The Russian authors report that vacuum therapy resulted in faster cleansing of the wound and more rapid detoxification than with the traditional incision-drainage method. The November 1986 Russian article describes the vacuum therapy techniques as a reduction of 0.8-1 atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76-114 mmHg. The Russian articles teach using this vacuum method to decrease the number of microbes in the wound. The June 1990 Russian article teaches that this vacuum therapy provides a significant antibacterial effect. The article describes the stepped up inflow of blood to the zone around the wound to lead to an increase in the number of leukocytes reaching the focus of inflammation. Subsequent articles and patents further develop the benefits obtained with vacuum therapy.

Retention discs for use with tubing are known as well. For example, Cook Urological Inc. manufactures a silicone retention disc used to stabilize indwelling catheters such as the Khonsari disc having order number VPI-052019, for example. These discs are supplied by Cook in sterile peel-open packages. Such retention discs are available in a variety of sizes to fit catheters having different outer diameters, for example.

Often, these external retention discs are used to prevent indwelling catheters from migrating inward after they have been implanted. Other devices are known in the art to prevent inward tube migration. See, for example, U.S. Pats. Nos. 5,374,254 and 5,484,420 which generally disclose retention bolsters for supporting catheters.

SUMMARY OF THE INVENTION

The present invention comprises one or more of the following features or combinations thereof:

A bandage connectable to a vacuum source or an irrigation source is provided for use with a wound having a wound surface. The bandage illustratively includes a flexible cover positioned over the wound and configured to seal with a patient's healthy skin surrounding the wound. The cover may include a port. The bandage may include a collar coupled to the cover, the collar including a passageway in communication with the port of the cover. The passageway may be configured to receive at least a portion of a tube in communication with the vacuum source or irrigation source. The bandage may further include a sealer coupled to the collar and configured to create an airtight seal between the tube and the passageway to create a sealed environment below the cover and above the wound surface.

The collar may include a disc and a tube receiver coupled to the disc. The tube receiver may include the passageway configured to receive a portion of the tube in communication with either the vacuum source or the irrigation source. The collar may be coupled to a top surface of the cover.

In illustrative embodiments, the collar may include a slit through the tube receiver and the disc portion extending from the passageway to an outer edge of the disc portion. This slit may be defined by a first end and a second end of the collar. The first and second ends normally engage each other so that the collar is in a closed position. The first and second ends move to an opened position spaced apart from each other when the tube is received in part within the passageway of the tube receiver.

In further embodiments, the sealer may be a pull-tab positioned around a neck portion of the tube receiver. The pull-tab tightens around the neck portion to move the collar from the opened position to the closed position to create a substantially airtight seal between the tube and the collar.

In another embodiment, the sealer may be a thin, elastic membrane covering the passageway of the collar. In use, the tube breaks the membrane when inserted into the passageway. The broken membrane creates a seal between the collar and the tube.

Other features of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
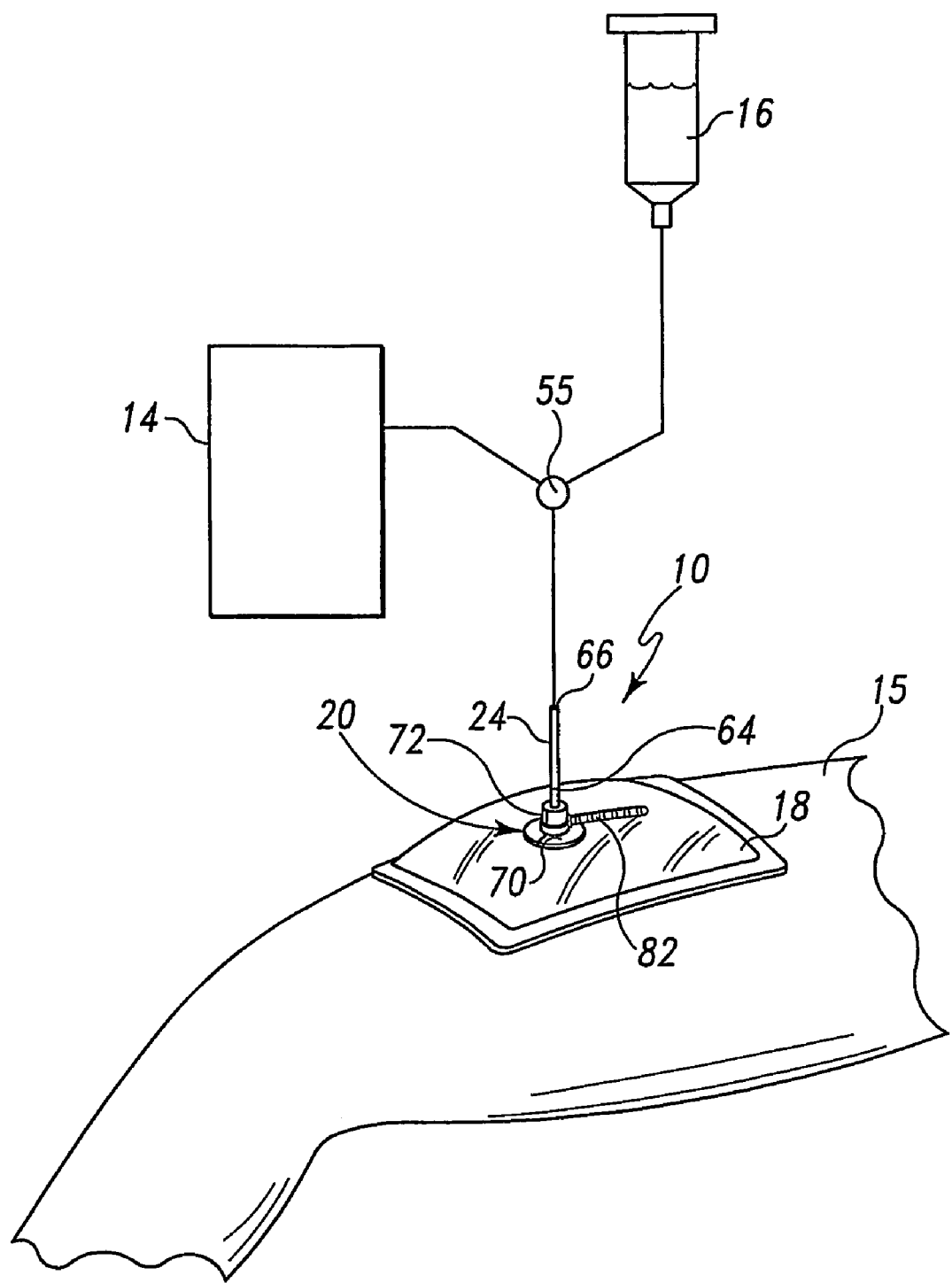
FIG. 1 is a part perspective, part diagrammatic view of a wound care bandage showing the wound care bandage located on the leg of a patient and coupled to both a vacuum source and an irrigation source through the use of a switch valve and further showing a collar positioned on top of the bandage.
Figure 2:
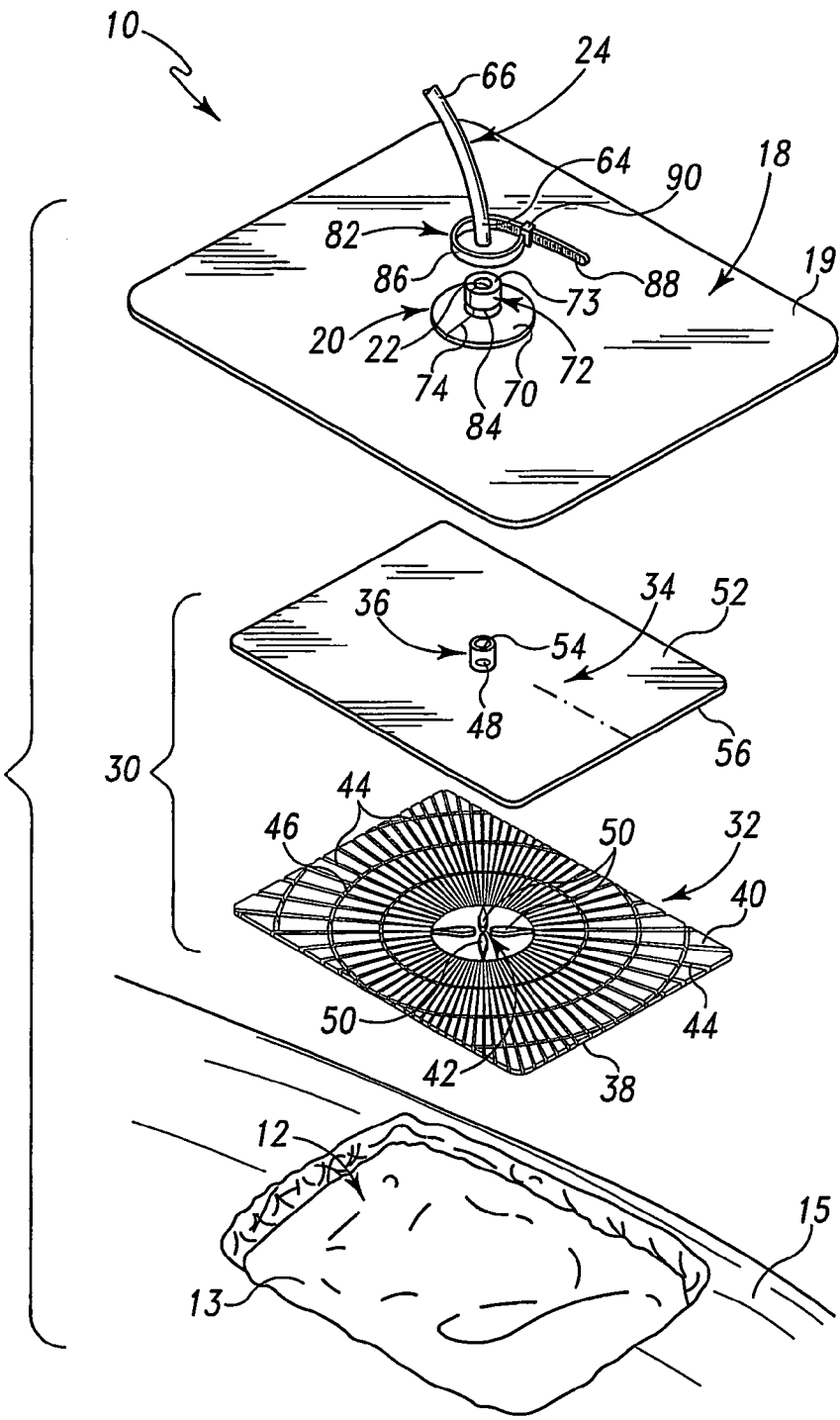
FIG. 2 is an exploded perspective view of the wound care bandage positioned above a wound bed showing a wound contacting layer and a cover of the bandage which cooperate to form a wound dressing member for placement within the wound bed, showing a sealing film or outer cover to cover the member and seal about the wound, and also showing the collar coupled to the outer cover to receive a portion of a vacuum/irrigation tube in communication with the vacuum source or the irrigation source.

A vacuum bandage 10 is provided for use with a wound 12 having a wound surface 13, as shown in FIG. 2. Vacuum bandage 10 is provided for use with a vacuum source 14 and an irrigation source 16, through the use of a switch valve 55, as shown, for example, in FIG. 1. Bandage 10 promotes the healing of wound 12 by providing vacuum therapy to the wound 12 to promote blood flow and remove exudate from wound surface 13 of the wound 12 and by providing for irrigation of the wound 12 with fluids such as saline, for example. Reference is made to U.S. Pat. No. 6,458,109 which discloses similar vacuum and irrigation treatment for wounds. This application is incorporated herein by reference. An illustrative vacuum and irrigation system is disclosed in U.S. Patent Publication No. US 2002/0161317 A1. Additionally, an illustrative vacuum bandage is disclosed in U.S. Patent Publication No. US 2002/0065494 A1. Each of these two applications is specifically incorporated herein by reference.

As shown in FIG. 1, bandage 10 includes a sealing film or outer cover 18 positioned above the wound 12 to seal to a patient's healthy slin 15 surrounding the wound 12 to create a sealed environment between the wound surface 13 and the outer cover 18 in which negative pressure or vacuum can be established. Bandage 10 further includes a collar 20 coupled to a top surface 19 of outer cover 18, as shown in FIGS. 1-5. Collar 20 includes a passageway 22 for receiving a portion of a vacuum/irrigation tube 24 in communication with the vacuum source 14 and/or the irrigation source 16. Collar 20 provides external catheter or tube access directly to wound surface 13 to provide wound surface 13 with irrigation and/or suction while maintaining an airtight environment around wound 12. Collar 20 is discussed in more detail below.

Figure 3:
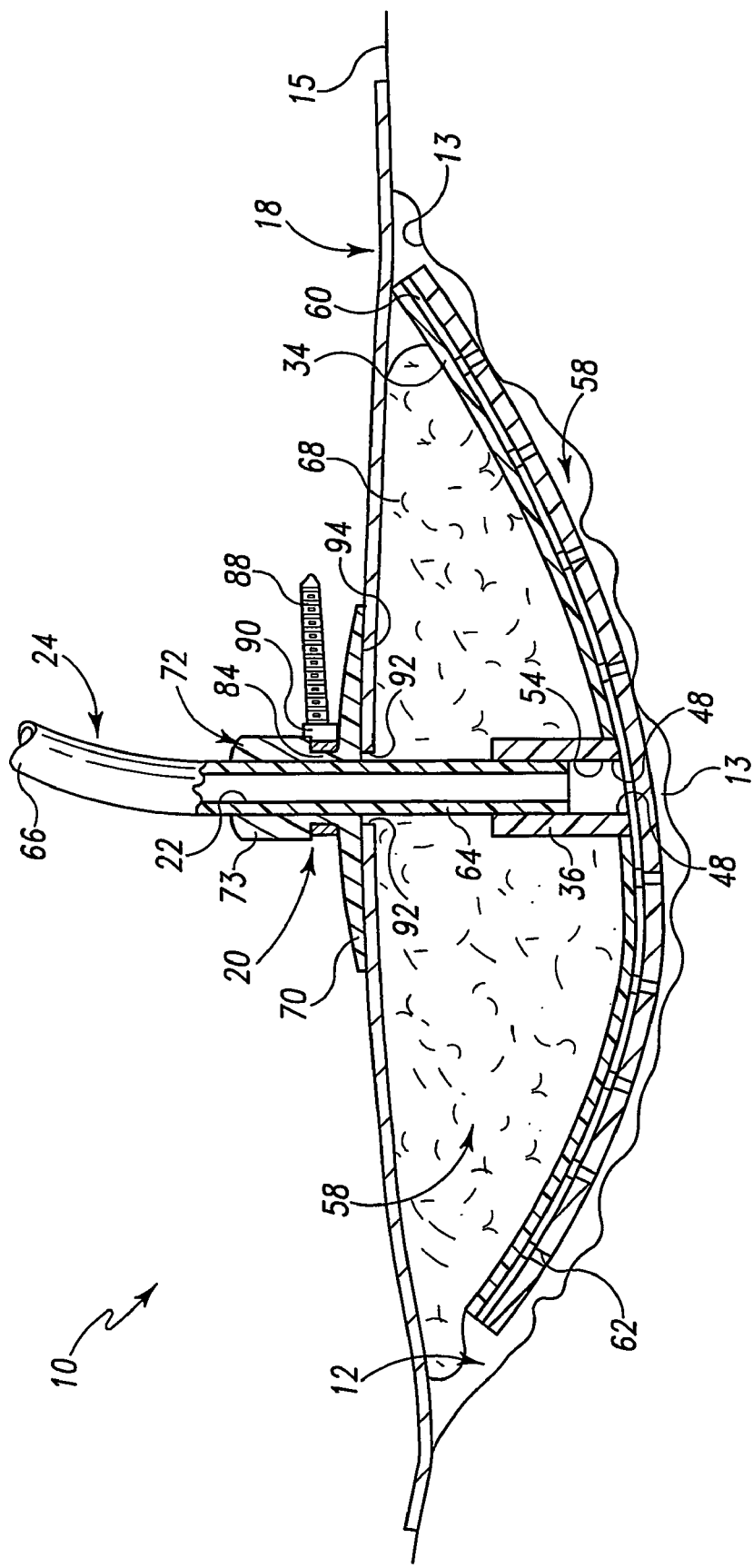
FIG. 3 is a sectional view of a bandage positioned within the wound bed and showing the film or outer cover of the bandage coupled to the healthy skin surrounding the bandage to create a sealed vacuum space above the wound and showing a portion of the vacuum/irrigation tube received in the collar and the outer cover and coupled to the member.

Looking now to FIG. 2, bandage 10 further includes a thin, flexible wound dressing member 30. Member 30 includes a wound contacting layer 32, a cover 34 coupled to the layer 32, and a connecter 36 coupled to cover 34 for communication with tube 24, as shown in FIG. 3. Member 30 is placed on wound 12 adjacent wound surface 13, as shown in FIG. 3. Outer cover 18 is placed over member 30 to cover the entire wound 12 and to extend across and attach to the patient's healthy skin 15, as described above.

Layer 32, cover 34, and connecter 36 of member 30 are each made of a medical grade silicone or other type of pliable elastomer. Two companies, for example, which manufacture such medical grade silicone are GE Silicones and NuSil Technology. It is within the scope of this disclosure, however, to include a member made of any type of thin, flexible material that is non-porous and non-foam-like. This thin, flexible material is also generally non-absorptive. For example, materials such as polyvinylchloride (PVC), PVC free of diethylhexyl phthalate (DEHP-free PVC), polyurethane, or polyethylene may be used in the manufacture of member 30. Further, layer 32, cover 34, and connecter 36 may each be molded to include anti-microbial constituents. For example, it is within the scope of this disclosure to impregnate member 30 with silver ions which are known anti-microbials.

Member 30, including layer 32, cover 34, and connecter 36, is also made of a generally non-adhesive material. Therefore, wound contacting layer 32, which lies adjacent to the wound surface 13, does not adhere to the wound surface 13. Further, member 30 is solid in nature and generally non-compressible. Member 30 is also transparent. Therefore, a caregiver or user is able to see the wound 12 through member 30 when member 30 is placed adjacent to wound surface 13. This transparency allows the caregiver to view the progress of the healing of the wound 12.

Layer 32 includes a wound-contacting surface 38 and an upper or opposite surface 40. Wound contacting surface 38, or portions thereof, contact and conform to the wound surface 13. Opposite surface 40 includes a central area 42 and a plurality of channels 44 spaced-apart from and extending radially away from central area 42. As shown in FIG. 2, opposite surface 40 further includes concentric channels 46. Illustratively, each channel 44, 46 is 0.030 inch (0.762 mm) wide and 0.030 inch (0.762 mm) deep. It is within the scope of this disclosure, however, to include channels 44, 46 of opposite surface 40 having various widths and depths suitable for the present application. Central area 42 of layer 32 is provided to communicate with the vacuum source 14 and irrigation source 16 through a port 48 of cover 34, as is described below.

A plurality of radially extending protrusions or bosses 50 are positioned around central area 42. Bosses 50 are positioned between central area 42 and channels 44, 46, as shown in FIG. 2. Bosses 50 are provided to prevent central area 42 from collapsing in on port 48 of cover 34 to form a seal and effectively block fluid flow through port 48 while suction is applied to bandage 10. Port 48, as shown in FIGS. 2 and 3, communicates with the vacuum source 14 and/or the irrigation source 16 via connecter 23, collar 20, and tube 24. It is within the scope of this disclosure for tube 24 to be coupled to connecter 36 by a barbed tube coupler (not shown) or to be coupled directly to connecter 36.

As mentioned above, port 48 is in communication with central area 42 of layer 32. Illustratively, four bosses 50 are shown in FIG. 2. However, it is within the scope of this disclosure to provide any number of bosses 50 or the like around central area 42 of layer 32 to prevent central area 42 from sealing off port 48 of cover 34 as suction is applied to bandage 10. Further, it is within the scope of this disclosure to include a boss or bosses having any shape in order to prevent central area 42 from sealing off port 48 when vacuum source 14 is running.

Connecter 36, as shown in FIGS. 2 and 3, is a tubal port coupled to a top surface 52 of cover 34. As mentioned above, it is within the scope of this disclosure for connecter 36 to be a separate component of member 30 which is coupled to cover 34 or for connecter 36 to be coupled to cover 34 by being molded integrally with cover 34. Connecter 36 includes a vertical passageway 54 that communicates with port 48 of cover 34. Connecter 36 connects with tube 24 to provide a vertical tube attachment for tube 24. Cover 34 includes a bottom surface 56 and top surface 52, as shown in FIG. 2, for example. Bottom surface 56 engages opposite surface 40 of layer 32, also shown in FIG. 2.

In some embodiments, member 30 is formed by heat sealing opposite surface 40 of layer 32 and bottom surface 56 of cover 34 together and by heat sealing connecter 36 to top surface 52 of cover 34. For example, each of layer 32, cover 34, and connecter 36 may be pre-shaped and formed from semi-cured silicone. Once the connecter 36, cover 34, and layer 32 are placed together appropriately, the entire member 30 may be heated to heat seal and cure each of the three components to one another. Alternatively, for example, the cover 34 only may be made from semi-cured silicone while the layer 32 and connecter 36 may be made from fully cured silicone, or visa versa. Once placed together and heated, connecter 36 and layer 32 will heat seal to cover 34. Semi-cured silicon may be bought and pre-molded from a manufacturer such as NuSil Technology, for example.

Although the method of heat sealing the connecter 36, cover 34, and layer 32 to each other is disclosed, it is within the scope of this disclosure to form member 30 by coupling layer 32, cover 34, and connecter 36 together by any other means such as through the use of adhesives, for example. Further, it is within the scope of this disclosure to provide a member 30 where the cover 34 lies adjacent to, but is not coupled to, the layer 32.

As mentioned above, cover 34 is coupled to layer 32 and connecter 36 is coupled to cover 34. Cover 34 and layer 32 cooperate to form distinct passageways 50 of member 30 defined by channels 44, 46 of layer 32 and bottom surface 56 of cover 34. Passageways 60 extend from the outer edges of member 30 and are in communication with central area 42 of layer 32. Central area 42 of layer 32 is in communication with port 48 of cover 34 which is in communication with the vacuum and/or irrigation sources 14, 16, via tube 24 extending through collar 20. Therefore, passageways 60 are in communication with the vacuum and/or irrigation sources 14, 16.

Layer 32 further includes through holes 62 which extend from channels 44, 46 to wound contacting surface 38, as shown in FIG. 2. Holes 62 are distinct and are provided to communicate with channels 44, 46 of layer 32. Holes 62 therefore communicate with passageways 60 of member 30 and the vacuum and/or irrigation sources 14, 16 as well to allow the suction from the vacuum source 14 and/or the fluid from the irrigation source 16 to reach the wound bed surface 13 via the holes 60. Illustratively, holes 62 are 0.020 inch (0.508 mm) in diameter and are spaced approximately 0.500 inch (12, 700 mm) apart along channels 44, 46 of layer 32. It is, however, within the scope of the disclosure to include holes having other suitable sized diameters and/or other suitable spacing that allow for the removal of exudate without generally clogging.

As mentioned above, bandage 10 further includes sealing film or outer cover 18. Outer cover 18 covers the entire wound 12 by extending over wound 12 and attaching to the patient's healthy skin 15 surrounding wound 12. Preferably, film or outer cover 18 is an occlusive or semi-occlusive material which allows water vapor to permeate though. Because of this characteristic, the outer cover 18 is referred to a Moisture Vapor Transmission Rate film or MVTR film. The products TEGADERM® brand sealing film made by 3M Corporation, and OPSITE FLEXIGRID® brand semi-permeable dressing made by Smith & Nephew can be used for outer cover 18, for example. Outer cover 18 is approximately 0.003 inch (0.076 mm) thick. However, it is within the scope of this disclosure to include any occlusive or semi-occlusive film or outer cover 18 having another thickness. Outer cover 18 is provided to create a sealed environment below the outer cover 18 and around the wound 12 in which a vacuum or negative pressure can be maintained as provided by vacuum source 14. Outer cover 18 therefore creates a vacuum space 58 between outer cover 18 and wound surface 13.

As shown in FIG. 3, bandage 10 may optionally include a packing material or filler 68, such as gauze, for example. Filler 68 is positioned between outer cover 18 and member 30. It is within the scope of this disclosure, however, for bandage 10 to not include filler 68. In other words, outer cover 18 would be positioned adjacent top surface 52 of cover 34 without any packing.

As shown in FIG. 3, member 30 of bandage 10 includes channels 47 formed in wound contacting surface 38. Wound contacting surface 38 may also be textured or roughened and/or may include a rib, protrusion, channel, or spacer design. By providing member 30 with a rib, protrusion, channel, or spacer, a space is created between surface 38 of layer 32 and wound surface 13. Through holes 62 communicate with this space to permit vacuum source 14 to establish a generally uniformly distributed vacuum or negative pressure to the wound surface 13 to draw blood from the body to the wound surface 13 and to draw exudate from the wound 12 through holes 62, into channels 44, 46 and passageways 60, and out port 48 of cover 34. It is also within the scope of this disclosure, however, to provide bandage 10 having a smooth wound contacting surface 38.

The vacuum or negative pressure which draws blood from the body to the wound surface 13 and draws exudate from the wound 12 up through member 30 promotes the healing of wound 12. As wound 12 heals, granulations form along the wound surface 13. Granulations, therefore, are the replacement within the wound bed of tissue lost. As the granulations fill in the wound bed causing the wound 16 to heal, member 30 rides up on the wound surface 13 on top of the granulations which are formed.

As mentioned above, port 48 of cover 34 communicates with vacuum source 14 and/or irrigation source 16 via connecter 36 and tube 24. As shown in FIG. 1, a switch valve 55 is provided which allows the caregiver to switch between the use of the vacuum source 14 and the irrigation source 16. It will be appreciated that a mechanism other than the switch valve 55 may be used selectively to couple the vacuum source 14 or the irrigation source 16 to the bandage 10. Simple tube clamps, for example, may be used selectively to open and close the tube set provided with bandage 10. When valve 55 is switched to operate the vacuum source 14, the vacuum suction draws exudate up through holes 62 and radially inwardly through passageways 60 toward port 48 and finally through connecter 36 and tube 24. Although tube 24 has been referred to as vacuum tube 24, tube 24 may also be used as an irrigation tube carrying liquid to the wound 12 from irrigation source 16, as described above.

Figure 4:
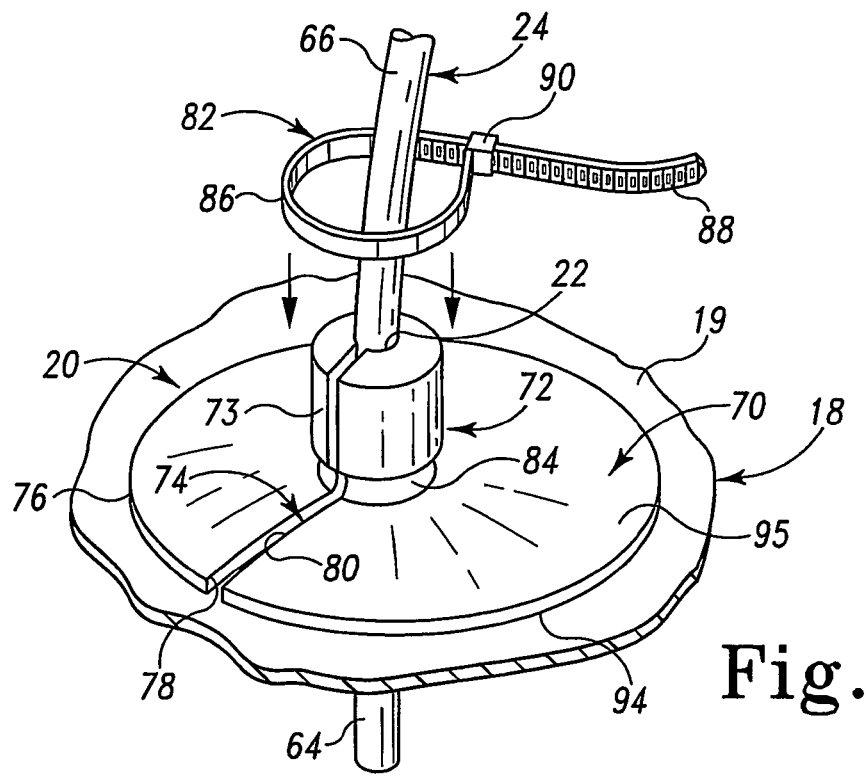
FIG. 4 is a perspective view with portions broken away showing the collar coupled to the outer cover, a portion of the tube received in the collar and the outer cover, a slit of the collar extending from an aperture of the collar to an outer edge or rim of the collar, and a pull-tab arranged for placement around a neck of the collar to tighten the collar about the tube.
Figure 5:
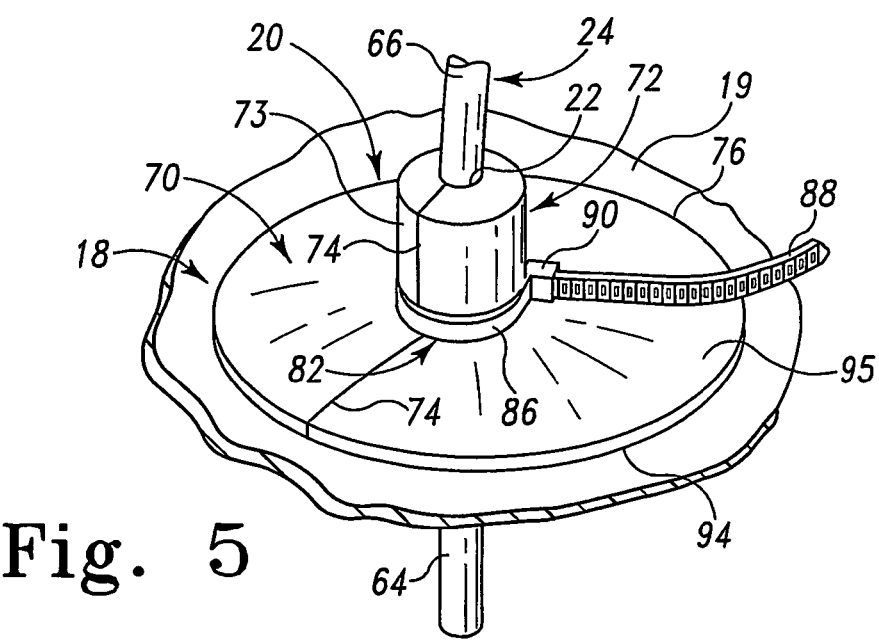
FIG. 5 is a perspective view similar to FIG. 4 showing the pull-tab around the neck of the collar and pulled tight around the neck to close the slit of the collar to create a substantially airtight seal between the collar and the tube.

As mentioned above, collar 20 is coupled to outer cover 18 and includes passageway 22 for receiving a portion of tube 24 therethrough, as shown in FIGS. 3-5. As shown in FIG. 1, tube 24 includes a first region 64, a portion of which is received in passageway 22 of collar 20, and a second region 66 in communication with the vacuum source 14 and/or the irrigation source 16. Collar 20 provides external catheter or tube 24 access to member 30. Collar 20 further provides a substantially airtight lock or seal between tube 24 and outer cover 18. As shown in FIGS. 2, 4, and 5, illustrative collar 20 is a retention disc. Various silicone retention discs are available commercially such as the Cook Urological Khonsari Retention Disc, for example. Collar 20 includes a generally flat disc portion 70 and a tube receiver 72 coupled to disc portion 70 and formed to define passageway 22 for receiving a portion of first region 64 of tube 24, as shown in FIG. 3.

Collar 20 includes a slit 74 from passageway 22 to an outer edge 76 of disc portion 70, as shown in FIG. 4. Collar 20 is normally in a closed position, as shown in FIG. 2, and is moved to an opened position, as shown in FIG. 4, where a first surface 78 and a second surface 80 of collar 20 are spaced apart from each other.

Collar 20 further includes a pull-tab 82, as shown in FIGS. 4 and 5. Pull-tab 82 is placed around a neck portion 84 of tube receiver 72, as shown in FIG. 4, and pulled tight around neck portion 84 to move collar 20 from the opened position to the closed position where first surface 78 and second surface 80 are adjacent to and engage each other, as shown in FIG. 5. Pull-tab 82 includes a strap 86 having a first end region including ridges 88 and a second end region coupled to a strap-retainer 90 of the pull-tab 82. A portion of the ridged end region of strap 86 extends through strap-retainer 90 so that pull-tab 82 forms a loop, as shown in FIG. 4. A head 73 of tube receiver 72 is placed through the loop of pull-tab 82 to position pull-tab 82 around neck portion 84 of tube receiver 72. A caregiver then pulls the ridged end of strap 86 further through strap-retainer 90 to reduce the size of the loop around neck portion 84 to cause collar 20 to move to the closed position. When pull-tab 82 is pulled tight, strap 86 engages neck portion 84 and is trapped between disc portion 70 and head 73.

As mentioned above, collar 20 is coupled to outer cover 18, as shown in FIGS. 3-5. Illustratively, collar 20 is coupled to top surface 19 of outer cover 18. Although top surface 19 of outer cover 18 is coupled to a bottom surface 94 of disc portion 70 of collar 20, it is within the scope of this disclosure to include a bandage where the outer cover 18 is coupled to any outer surface of the collar 20, such as a top surface 95 of disc portion 70, for example, so that outer cover 18 and collar 20 are coupled to each other in a substantially airtight manner. It is within the scope of this disclosure, however, to include a bandage having a collar coupled to an outer cover using any suitable means such an adhesive or adhesives or by heat sealing the outer cover to the collar, for example. It is further within the scope of this disclosure to include a bandage where the collar and the outer cover are manufactured as one component for receiving first end 64 of tube 24 therethrough and for covering wound 12 to attach to the patient's healthy skin 15 surrounding wound 12. As shown in FIG. 3, outer cover 18 further includes an aperture 92 for receiving a portion of first end region 64 of tube 24 therein, as shown in FIG. 3. Aperture 92 of outer cover 18 is aligned with passageway 22 of tube receiver 72 of collar 20 so that tube 24 is able to extend through collar 20 and outer cover 18 to communicate with wound 12 through member 30.

To dress wound 12, a caregiver places member 30 adjacent the wound surface 13. Specifically, wound-contacting surface 38 of layer 32 is placed adjacent wound surface 13. Packing or filler 68 may then be placed over member 30 and wound surface 13, if desired. (However, in many cases, caregivers will not use such packing.) Outer cover 18 and collar 20 coupled to outer cover 18 are next placed over the filler 68, if used, or directly over member 30 adjacent top surface 52 of cover 34. Outer cover 18 is attached to the patient's healthy skin 15 surrounding wound 12, as shown in FIG. 3. First end 64 of tube 24 is then inserted through passageway 22 of tube receiver 72 and aperture 92 of outer cover 18 into vacuum space 58 created by bandage 10. The caregiver then couples tube 24 to connecter 36 of member 30.

The caregiver may wish to align connecter 36 of member 30 with the already aligned aperture 92 of outer cover 18 and passageway 22 of collar 20 in order to be able to more easily couple first end 64 of tube 24 to connecter 36 once tube 24 is inserted through collar 20 and outer cover 18. Once tube 24 is coupled to connector 36, caregiver tightens pull-tab 82 by pulling the ridged end region of strap 86 through strap-retainer 90 until collar 20 is in the closed position having first surface 78 and second surface 80 clamped together. In the closed position, with pull-tab 82 tightened around neck portion 84, collar 20 creates a substantially airtight seal between tube 24 and film 18. Pull-tab 82 can be loosened by the caregiver to allow the caregiver to remove tube 24 if desired. Thus, collar 20 provides for external access through outer cover 18 of wound 12 without the need to remove outer cover 18. Collar 20 also maintains a substantially airtight environment when tube 24 extends through collar 20 and outer cover 18.

Figure 6:
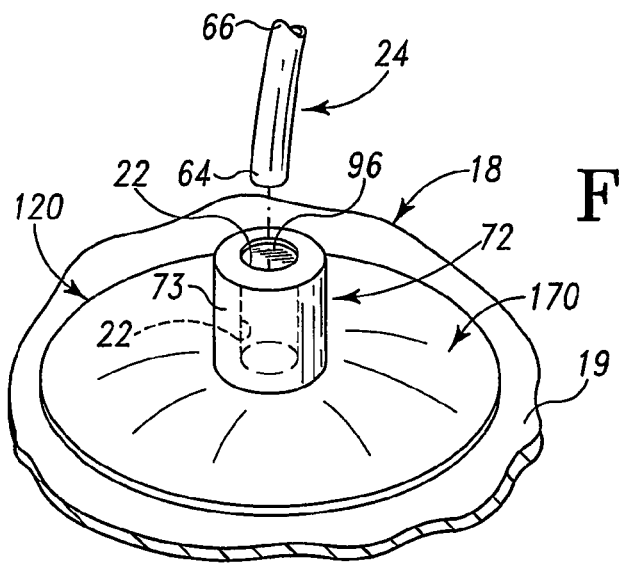
FIG. 6 is a perspective view of an alternative collar of the wound care bandage of the present disclosure showing the alternative collar formed without the slit shown in the previous embodiment and including a thin, elastic membrane across the opening or aperture of the collar.
Figure 7:
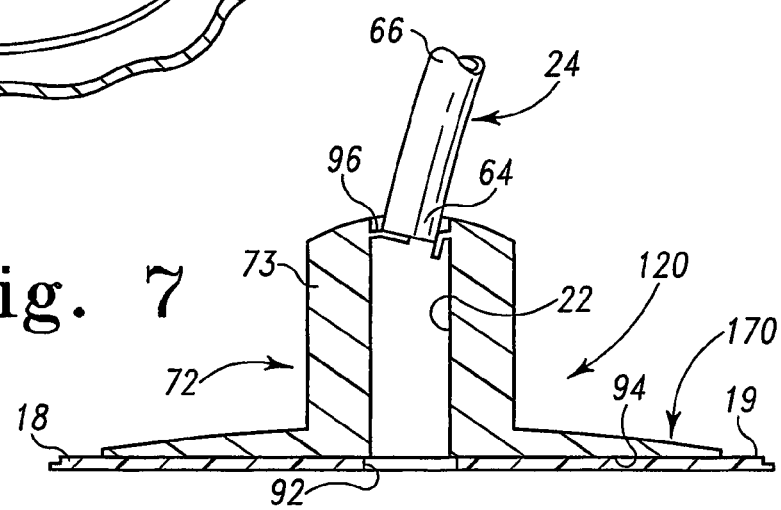
FIG. 7 is a sectional view of the alternative collar of FIG. 6 showing the vacuum/irrigation tube being pushed through the membrane to break the membrane while a portion of the tube is inserted through the collar.
Figure 8:
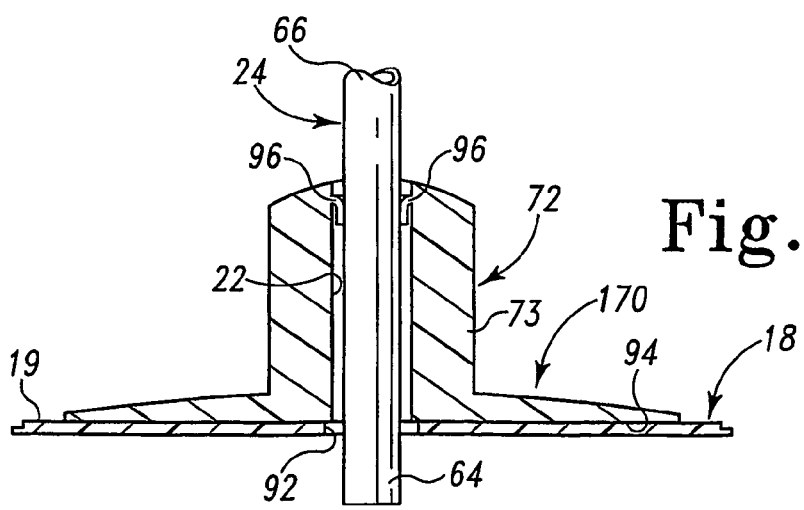
FIG. 8 is a sectional view similar to FIG. 7 showing a portion of the tube extending through the collar and showing the broken membrane forming a substantially airtight seal between the tube and the collar.

Referring now to FIGS. 6-8, another illustrative embodiment of a collar 120 is shown as a component of bandage 10. Collar 120 is similar to collar 20 and as such, the same reference numerals have been used in FIGS. 6-8 to designate similar components to those components previously discussed in regard to FIGS. 1-6. Therefore, additional discussion thereof is not warranted.

One difference between collar 120 and collar 20 is that collar 120 does not include slit 74 defined by first surface 78 and second surface 80. A disc portion 170 therefore of collar 120 does not move between an opened position and a closed position as disc portion 70 does. However, collar 120 includes a thin, elastic membrane 96 across passageway 22 of tube receiver 72, as shown in FIG. 6, for example. In use, the caregiver pushes first end 64 of tube 24 through passageway 22 to break or tear membrane 96. The broken membrane then acts to create a substantially airtight seal between tube 24, neck portion 84 of collar 20, and outer cover 18 without the need for pull-tab 82. Therefore, collars 20 and 120 each provide a substantially airtight seal between outer cover 18 and tube 24 while allowing a caregiver to remove and replace tube 24 without the need to remove and reseal outer cover 18 around wound 12. Pull-tab 82 and membrane 96 each act as a sealer of collars 20, 120, respectively, to create a seal between tube 24 and collar 20, 120.

Although this invention has been described in detail with reference to certain embodiments, variations and modifications exist within the scope and spirit of the invention as described and defined in the following claims.

The invention claimed is:

1. A bandage connectable to a vacuum source for use with a wound having a wound surface, the bandage comprising
  a flexible cover positioned over the wound and configured to seal to a patient's healthy skin surrounding the wound, the cover including a port,
  a collar coupled to the cover and including a passageway in communication with the port of the cover, the passageway being configured to receive at least a portion of a tube in communication with the vacuum source,
  a sealer coupled to the collar and configured to provide a substantially airtight seal between the tube and the passageway to create a sealed environment capable of maintaining a negative pressure between the cover and the wound surface, and
  a flexible member positioned to lie directly adjacent the wound surface, the member including a connector configured to receive the tube.

2. The bandage of claim 1, wherein the collar includes a disc portion coupled to the cover and a tube receiver coupled to the disc portion, and wherein the tube receiver extends away from the cover and includes the passageway in communication with the port of the cover.

3. The bandage of claim 2, wherein the tube receiver includes a narrow neck portion adjacent the disc portion.

4. The bandage of claim 3, wherein collar includes a slit formed through the tube receiver and the disc portion and extending outwardly from the passageway to an outer edge of the disc portion to define radially extending first and second surfaces, and wherein the collar is normally in a closed position, where first and second surfaces are adjacent each other and is moved to an opened position, where the first surface and the second surface are spaced apart from each other, to configure the collar to receive the tube at least in part into the passageway.

5. The bandage of claim 4, wherein the sealer is a pull-tab positioned around the neck portion and configured to be tightened around the neck portion to move the slit from the opened position to the closed position.

6. The bandage of claim 1, wherein the collar is coupled to a top surface of the cover.

7. A vacuum bandage connectable to a vacuum source for providing vacuum treatment to a wound having a wound surface, the vacuum bandage comprising
  a synthetic flexible member positioned to lie directly adjacent the wound surface, the member including a connector configured to receive a vacuum tube to couple the tube to the member, the vacuum tube in communication with the vacuum source,
  a thin, flexible cover positioned over the member and configured to seal to a patient's healthy skin surrounding the wound, the cover including a port, and
  a collar coupled to the cover and including a passageway in communication with the port of the cover, the passageway being configured to receive at least a portion of the vacuum tube in communication with the vacuum source or irrigation source, and the collar configured to permit the tube to be removed and replaced while the cover remains sealed to the patient's healthy skin surrounding the wound.

8. The bandage of claim 7, wherein the collar includes a disc portion and a tube receiver coupled to the disc portion and including the passageway.

9. The bandage of claim 8, wherein the collar is coupled to the top surface of the cover.

10. The bandage of claim 7, ffirtber including a means for creating a generally airtight seal between the tube and the collar.

11. The bandage of claim 10, wherein the means is a pull-tab for placement around the passageway of the collar, the pull-tab is adjustable about the collar to increase and decrease the size of the passageway within in which the tube is at least in part received.

12. The bandage of claim 11, wherein the pull-tab includes a strap having ridges at one end and a strap retainer coupled to the other end and the ridged end is received through the strap retainer to create a loop around the collar.

* * * * *